United States Patent
Li et al.

(10) Patent No.: US 9,987,324 B2
(45) Date of Patent: Jun. 5, 2018

(54) TRADITIONAL CHINESE MEDICINE COMPOSITION AND THE USE THEREOF

(71) Applicant: INFINITUS (CHINA) COMPANY LTD., Jiang Men, Guangdong (CN)

(72) Inventors: Jiangping Li, Jiang Men (CN); Shiyu Zou, Jiang Men (CN); Chung Wah Ma, Jiang Men (CN)

(73) Assignee: INFINITUS (CHINA) COMPANY LTD., Jiang Men, Guangdong (CN)

(*) Notice: Subject to any disclaimer, the term of this patent is extended or adjusted under 35 U.S.C. 154(b) by 205 days.

(21) Appl. No.: 15/164,861

(22) Filed: May 25, 2016

(65) Prior Publication Data

US 2016/0375084 A1    Dec. 29, 2016

(30) Foreign Application Priority Data

Jun. 29, 2015    (CN) .......................... 2015 1 0372956

(51) Int. Cl.
| | |
|---|---|
| *A61K 36/00* | (2006.01) |
| *A61K 36/8967* | (2006.01) |
| *A61K 36/73* | (2006.01) |
| *A61K 36/60* | (2006.01) |
| *A61K 36/89* | (2006.01) |
| *A61K 36/42* | (2006.01) |
| *A61K 36/736* | (2006.01) |
| *A61K 35/644* | (2015.01) |
| *A23L 2/02* | (2006.01) |
| *A23L 2/52* | (2006.01) |
| *A23L 33/105* | (2016.01) |

(52) U.S. Cl.
CPC ............ *A61K 36/8967* (2013.01); *A23L 2/02* (2013.01); *A23L 2/52* (2013.01); *A23L 33/105* (2016.08); *A61K 35/644* (2013.01); *A61K 36/42* (2013.01); *A61K 36/60* (2013.01); *A61K 36/73* (2013.01); *A61K 36/736* (2013.01); *A61K 36/89* (2013.01)

(58) Field of Classification Search
CPC ....................................................... A61K 36/00
USPC ....................................................... 424/725
See application file for complete search history.

(56) References Cited

FOREIGN PATENT DOCUMENTS

| CN | 101991031 A | 3/2011 |
|---|---|---|
| CN | 103461870 A | 12/2013 |
| CN | 103653085 A | 3/2014 |
| CN | 103749779 A | 4/2014 |
| CN | 104041873 A | 9/2014 |

OTHER PUBLICATIONS

The Big Efficiency of Little Edible Material, The 1st edition, Yang Li, Jiangsu science tech publishing house, the pp. 172-173, In Mar. 2014.
The Practical Therapy of the Tumour Traditional Chinese Medical Science, The 1st edition, Zhou,Hongjin, the Golden Shield Press, p. 295, In Feb. 2014.
The Chinese 1st Office Action for CN201510372956.9, dated Sep. 1, 2016.

*Primary Examiner* — Michael V Meller
(74) *Attorney, Agent, or Firm* — U.S. Fairsky LLP; Yue Xu

(57) ABSTRACT

The present invention relates to the technical field of Chinese medicine, in particular to a traditional Chinese medicine composition and the use thereof. The traditional Chinese medicine composition comprises the following ingredients: pear juice, greenish lily bulb juice, fig juice, water chestnut juice, grosvenor momordica fruit, southern almond and northern almond. The traditional Chinese medicine composition has significant promotions on the phlegm-reducing and cough-relieving capabilities of the rats, and on the immune indices of bronchoalveolar lavage fluid of the rats, exhibiting that the traditional Chinese medicine composition provided in the present invention has good effects of clearing heat and moistening the lungs.

8 Claims, No Drawings

TRADITIONAL CHINESE MEDICINE COMPOSITION AND THE USE THEREOF

FIELD OF THE INVENTION

The present invention relates to the technical field of traditional Chinese medicine, in particular to a traditional Chinese medicine composition and the use thereof

BACKGROUND OF THE INVENTION

Seasonal change and increasingly severe environmental pollutions in cities are all impairing our respiratory systems to different extent. Meanwhile, for modern people the lack of outdoor exercise deprives their lungs of the opportunity to inhale fresh air; and the pollution by electronic office equipments in the offices easily leads to diseases such as allergies in the lungs, bronchial asthma and the like, as well as decreased resistance of the lungs. While there is an increasing demand for natural and healthy juice beverage with the effects of clearing heat and moistening the lungs, or other types of healthy food with the improvement of people's living standards and health consciousness, currently most of the juice beverage on the market is formulated by the addition of various flavors, fragrances, artificial sweeteners and pigments with low juice content and inappropriate formulation design, where the artificial sweeteners and pigments added even become disadvantages to the health, and the inappropriate formulation design lacks the factors regarding health concept, with little regulation to the symptoms in the lungs in everyday life; as most of the health food on the market has little effect on the treatment of the symptoms in the lungs, the provision of juice beverage or other types of health food that clear heat and moisten the lungs may fill the gap in the market.

The patent document with a patent publication number of CN 104041873 A discloses sugared pear juice consisting of 100-120 parts of pear, 30-35 parts of apple, 70-80 parts of crystal sugar, 200-220 parts of soybean milk, 20-30 parts of white fungus, 20-30 parts of almond, 8-10 parts of greenish lily bulb, 5-6 parts of grosvenor momordica fruit, 4-5 parts of pepperweed seed, 5-6 parts of loquat leaf, 3-4 parts of sessile stemona root, 4-5 parts of cochinchinese asparagus root, 2-3 parts of tatarian aster root and rhizome, 2-3 parts of garden burnet root, 8-10 parts of food additive and appropriate amount of water; the food additive is prepared by the following ingredients based on part by weight: 8-10 parts of corn smut powder, 5-7 parts of spirulina, 5-7 parts of japanese pagodatree flower, 30-40 parts of water caltrop, 30-40 parts of dictyophora indusiata, 4-5 parts of water caltrop stem, 50-60 parts of honey, 60-70 parts of rice wine and appropriate amount of water; the method for preparing the food additive is as follows: (1) the corn smut powder, the spirulina and the japanese pagodatree flower are extracted with 5-8 times more water to obtain the extract standby; (2) the water caltrop was peeled and then put into a pot with dictyophora indusiata, and after the addition of water caltrop stem, rice wine, honey and appropriate amount of water, all theses materials in the pot are heated and cooked before pulping into the juice standby; (3) the extract and the juice described above are combined and filtered after mixing evenly to obtain the filtrate standby. The sugared pear juice has the effects of promoting liquid production, moistening dryness, clearing heat, elimination phlegm, nourishing the heart, benefiting Qi, promoting liquid production and relieving cough and is delicious and nutritious.

The patent document with a patent publication number of CN 103461870 A discloses a pear syrup candy prepared by the ingredients including sugar, pear, isatis, fritillary, ternate, sessile stemona root, almond, licorice, grosvenor momordica fruit and ethyl maltol. The pear syrup candy has the effects of benefiting Qi, clearing fire, improving eyesight, nourishing the kidney, relieving sore throat and asthma, and moistening the lungs, with a strong fruity fragrance.

However, the patented products described above have suboptimal effects of clearing heat and moistening the lungs, failing to meet the needs of modern people.

For the reasons above, the development of health food that has significant effects of clearing heat and moistening the lungs to meet the needs of modern people has important practical significance.

SUMMARY OF THE INVENTION

In view of this, the present invention provides a traditional Chinese medicine composition and the uses thereof The traditional Chinese medicine composition has significant promotions on the phlegm-reducing and cough-relieving capabilities of the rats, and the immune indices of bronchoalveolar lavage fluid of the rats, exhibiting that the traditional Chinese medicine composition provided in the present invention has good effects of clearing heat and moistening the lungs. The present invention employs choice traditional Chinese medicine and food ingredients: pear juice, apple juice, greenish lily bulb juice, fig juice, water chestnut juice, grosvenor momordica fruit, southern almond, northern almond, crystal sugar and honey without the addition of flavor and fragrance, artificial sweeteners and pigments, resulting in a high juice content, abundant nutrition and unique taste.

To achieve the above objects of the invention, the present invention provides the following technical solutions:

The present invention provides a traditional Chinese medicine composition comprising the following ingredients:

Pear juice, greenish lily bulb juice, fig juice, water chestnut juice, grosvenor momordica fruit and/or grosvenor momordica fruit extract, southern almond and northern almond.

Pear: pear is delicious, crisp, juicy, sour, sweet and fragrant. It is rich in sugar, proteins, fat, hydrocarbons and various vitamins, and has important effects on human health with the ability to moisten the lungs, reduce phlegm, relieve cough, relieve constipation and help digestion. Pear is also a good medicine to treat diseases, for example, in the civil society pear stewed with sugar is often used to treat asthma and cough, and "pear syrup" is famous even throughout the world. Pear also has the effects of lowering blood pressure and clearing heat, thus of great benefit for patients with hypertension and heart disease.

Southern almond, northern almond: southern almond and northern almond are among the first medicinal and edible traditional Chinese medicines approved by Chinese Ministry of Health, wherein southern almond, also known as sweet almond, is edible as fruit and has the effects of moistening the lungs, relieving cough, moistening dryness, benefiting the lungs and nourishing the skin according to "Chinese Pharmacopoeia"; northern almond, also known as bitter almond, has the effects of lowering Qi, relieving cough and asthma, moistening the intestine and relaxing the bowels according to "Chinese Pharmacopoeia". Both the two almonds have the effects of relieving cough and asthma, wherein northern almond has stronger effects of relieving cough and asthma, while southern almond has slower efficacy but more significant effects of moistening the intestine and relaxing the bowels, and the combination of the two will improve the coordinative effects.

Grosvenor momordica fruit: according to the records in "Chinese Pharmacopoeia": grosvenor momordica fruit that is sweet and cool goes to the lung and large intestine channels; it has the effects of clearing heat, moistening the lungs, lubricating the intestine and relaxing the bowels, and may be used for the treatment of lung-fire dryness cough, intestinal dryness and constipation. It is mostly used to treat symptoms such as pertussis, phlegm-fire cough, blood dryness and constipation; it also has good therapeutic effects in the treatment of acute bronchitis, acute tonsillitis, throat-fire and acute gastritis; soaking a little grosvenor momordica fruit with boiled water produces an excellent refreshing drink, which may refresh oneself, promote the liquid production, prevent respiratory tract infections, and even prolong life if taken regularly; grosvenor momordica fruit juice that may be used in cooking is fragrant and delicious, so grosvenor momordica fruit is often known as "fairy fruit". Modern medicinal research has found that grosvenor momordica fruit is rich in glycoside, which has sweetness 300 times higher than that of sucrose, and has the effect of lowering blood sugar to be used to aid in the treatment of diabetes; modern research also shows that grosvenor momordica fruit has the effects of lowering blood lipid and losing weight, and thus may be used to aid in the treatment of hyperlipoidemia or to improve images of the obese population as the choice of pretty-looking women.

Fig: fig is one of the first domesticated and cultivated fruits in the world, and is always regarded as valuable health food, also known as "holy fruit". According to the records in the earliest "Sheng Nong's Herbal Classic" in China, fig that is sweet and flat has the effects of nourishing, clearing heat, moistening the lungs and treating sore throat, asthma and cough without toxic and side effects, thus widely spread in the civil society. Meanwhile, fig is rich in vitamins with a relatively higher content of vitamin C, and according to the measurements, the content of vitamin C is 2.3 times higher than that of orange, 8 times higher than that of peach and 20 times higher than that of grape.

Greenish lily bulb: greenish lily bulb has been used to treat diseases by traditional Chinese medicine for a history of over 2,000 years, first recorded in "Sheng Nong's Herbal Classic", "Rihuazi Materia Medica", "Supplement to Compendium of Materia Medica" and the like, and greenish lily bulb is not only delicious, but also has abundant nutrition and high medicinal value. Greenish lily bulb that is sweet and cold goes to the lung and heart channels, and has the effects of moistening the lungs, relieving cough, calming the mind, tranquillizing, nourishing the middle energizer and benefiting Qi. According to the pharmacological research, greenish lily bulb may increase the hemoperfusion in the lungs and improve the pulmonary function. Greenish lily bulb may also be used to treat the symptoms such as lung heat, lung dryness, cough, haemoptysis, low fever, deficiency of vital energy and the like. With the research on the chemical composition and pharmacology of greenish lily bulb, it is further found that the greenish lily bulb glycoside contained in greenish lily bulb has the effects of sedation and tranquillizing, so long-term use of greenish lily bulb acts to help sleeping and improve sleeping quality.

Water chestnut: water chestnut (scientific name: Eleocharis dulcis) with black peel and white flesh is sweet, juicy, crisp and delicious, also called "underground pear" or "south ginseng" by the north, and may be eaten raw like fruits or taken like vegetables as a popular seasonal food. Water chestnut that is cold in nature has the effects of clearing heat, detoxicating, cooling the blood, promoting liquid production, helping urination, relaxing the bowels, eliminating dampness, reducing phlegm, helping digestion and relieving flatulence, and may be used in the treatment of the diseases such as jaundice, dysentery, poliomyelitis, constipation and the like; water chestnut has an antibacterial component, which has certain effects of lowering blood pressure and preventing cancer. "Dietetic materia medica": "Water chestnut expels stones, eliminates wind-toxins, and removes excess heat in the chest. It may be taken in the form of powder. It improves eyesight, relieves thirst and eliminates jaundice. It cannot be taken in the presence of existing cold-Qi in that abdominal distention may occur. Children will have an ache below the umbilicus when eating it in autumn" "The mirror of medicine by Luo": "Water chestnut benefits Qi, tranquillizes the middle energizer, acts as an appetizer, helps digestion, clears heat, promotes liquid production, prevents dysentery, relieves thirst, and treats jaundice and bleeding."

In the present invention, a traditional Chinese medicine composition is prepared without the addition of flavors, fragrances, artificial sweeteners and pigments, using pear juice, greenish lily bulb juice, fig juice, water chestnut juice, grosvenor momordica fruit, southern almond and northern almond as the main ingredients based on the traditional Chinese medicine theory by adding choice medicinal and edible traditional Chinese medicine and natural and healthy food ingredients through scientific formulation design, and the obtained traditional Chinese medicine compositions of the present invention with a high content of juice have the effects of clearing heat and moistening the lungs.

In some examples provided in the present invention, the following components are included based on part by weight,

| | |
|---|---|
| Pear juice | 5 to 15 parts |
| Greenish lily bulb juice | 0.5 to 5 parts |
| Fig juice | 0.5 to 5 parts |
| Water chestnut juice | 0.5 to 5 parts |
| Grosvenor momordica fruit | 0.75 to 6 parts |
| Southern almond | 0.5 to 5 parts |
| Northern almond | 0.5 to 5 parts. |

In further examples provided in the present invention, the following components are included based on part by weight,

| | |
|---|---|
| Pear juice | 5 to 15 parts |
| Greenish lily bulb juice | 0.5 to 5 parts |
| Fig juice | 0.5 to 5 parts |
| Water chestnut juice | 0.5 to 5 parts |
| Grosvenor momordica fruit extract | 0.15 to 0.6 parts |
| Southern almond | 0.5 to 5 parts |
| Northern almond | 0.5 to 5 parts. |

In further examples provided in the present invention, the following components are included based on part by weight,

| | |
|---|---|
| Pear juice | 5 to 15 parts |
| Greenish lily bulb juice | 0.5 to 5 parts |
| Fig juice | 0.5 to 5 parts |
| Water chestnut juice | 0.5 to 5 parts |
| Grosvenor momordica fruit extract | 0.05 to 0.1 parts |
| Grosvenor momordica fruit | 0.5 to 5 parts |
| Southern almond | 0.5 to 5 parts |
| Northern almond | 0.5 to 5 parts. |

The present invention also provides a method for preparing the traditional Chinese medicine composition comprising the steps of:

The grosvenor momordica fruit, the southern almond and the northern almond are mixed and extracted with water to obtain an extract;

The pear juice, the greenish lily bulb juice, the fig juice, the water chestnut juice, the grosvenor momordica fruit extract and the extract described above are mixed to obtain the traditional Chinese medicine composition.

In some examples provided in the present invention, the traditional Chinese medicine composition further comprises apple juice.

Apple: apple is able to "moisten the lungs, delight the heart, promote fluid production and act as an appetizer", and has good nourishing and moistening effects on the lungs, with fragrance to help relieve mental depression. Meanwhile, apple has abundant nutrition including proteins, fat, hydrocarbons and various vitamins Preferably, the following components are included based on part by weight,

| | |
|---|---|
| Pear juice | 5 to 15 parts |
| Apple juice | 25 to 35 parts |
| Greenish lily bulb juice | 0.5 to 5 parts |
| Fig juice | 0.5 to 5 parts |
| Water chestnut juice | 0.5 to 5 parts |
| Grosvenor momordica fruit extract | 0.05 to 0.1 parts |
| Grosvenor momordica fruit | 0.5 to 5 parts |
| Southern almond | 0.5 to 5 parts |
| Northern almond | 0.5 to 5 parts. |

The present invention also provides a method for preparing the traditional Chinese medicine composition comprising the steps of:

The grosvenor momordica fruit, the southern almond and the northern almond are mixed and extracted with water to obtain an extract;

The apple juice, the pear juice, the greenish lily bulb juice, the fig juice, the water chestnut juice, the grosvenor momordica fruit extract and the extract described above are mixed to obtain the traditional Chinese medicine composition.

In some examples provided in the present invention, the traditional Chinese medicine composition further comprises crystal sugar.

Crystal sugar: crystal sugar that is sweet and flat goes into the lung and spleen channels; it has the effects of nourishing the middle energizer, benefiting qi, regulating the stomach and moistening the lung; and crystal sugar nourishes Yin, promotes fluid production, moistens the lung and relieves cough, and has excellent effects of helping in the treatment of lung dryness and cough, dry cough without sputum and cough with bloody sputum. In the civil society, people of all ages use crystal sugar when cooking a variety of nourishing food.

Preferably, the following components are included based on part by weight,

| | |
|---|---|
| Pear juice | 5 to 15 parts |
| Greenish lily bulb juice | 0.5 to 5 parts |
| Fig juice | 0.5 to 5 parts |
| Water chestnut juice | 0.5 to 5 parts |
| Grosvenor momordica fruit extract | 0.05 to 0.1 parts |
| Grosvenor momordica fruit | 0.5 to 5 parts |
| Southern almond | 0.5 to 5 parts |
| Northern almond | 0.5 to 5 parts |
| Crystal sugar | 5 to 10 parts. |

The present invention also provides a method for preparing the traditional Chinese medicine composition comprising the steps of:

The grosvenor momordica fruit, the southern almond and the northern almond are mixed and extracted with water to obtain an extract;

The crystal sugar, the pear juice, the greenish lily bulb juice, the fig juice, the water chestnut juice, the grosvenor momordica fruit extract and the extract described above are mixed to obtain the traditional Chinese medicine composition.

Preferably, the following components are included based on part by weight,

| | |
|---|---|
| Pear juice | 5 to 15 parts |
| Apple juice | 25 to 35 parts |
| Greenish lily bulb juice | 0.5 to 5 parts |
| Fig juice | 0.5 to 5 parts |
| Water chestnut juice | 0.5 to 5 parts |
| Grosvenor momordica fruit extract | 0.05 to 0.1 parts |
| Grosvenor momordica fruit | 0.5 to 5 parts |
| Southern almond | 0.5 to 5 parts |
| Northern almond | 0.5 to 5 parts |
| Crystal sugar | 5 to 10 parts. |

The present invention also provides a method for preparing the traditional Chinese medicine composition comprising the steps of:

The grosvenor momordica fruit, the southern almond and the northern almond are mixed and extracted with water to obtain an extract;

The crystal sugar, the apple juice, the pear juice, the greenish lily bulb juice, the fig juice, the water chestnut juice, the grosvenor momordica fruit extract and the extract described above are mixed to obtain the traditional Chinese medicine composition.

In some examples provided in the present invention, the traditional Chinese medicine composition further comprises honey.

Honey: "Chinese Pharmacopoeia" records: Honey is sweet and flat. It goes into the lung, spleen and large intestine channels. It has the effects of invigorating the middle energizer, moistening dryness, relieving pain and detoxicating, as well as promoting granulation and astringing sores when used externally. It may be used in the treatment of abdominal pain, lung dryness and cough, intestine dryness and constipation, and intoxication by aconitum; it may also be used in the treatment of sore and ulcer that are not astringed, and scald by water and fire when used externally.

Preferably, the following components are included based on part by weight,

| | |
|---|---|
| Pear juice | 5 to 15 parts |
| Greenish lily bulb juice | 0.5 to 5 parts |
| Fig juice | 0.5 to 5 parts |
| Water chestnut juice | 0.5 to 5 parts |
| Grosvenor momordica fruit extract | 0.05 to 0.1 parts |
| Grosvenor momordica fruit | 0.5 to 5 parts |
| Southern almond | 0.5 to 5 parts |
| Northern almond | 0.5 to 5 parts |
| Honey | 5 to 10 parts. |

The present invention also provides a method for preparing the traditional Chinese medicine composition comprising the steps of:

The grosvenor momordica fruit, the southern almond and the northern almond are mixed and extracted with water to obtain an extract;

The honey, the pear juice, the greenish lily bulb juice, the fig juice, the water chestnut juice, the grosvenor momordica fruit extract and the extract described above are mixed to obtain the traditional Chinese medicine composition.

Preferably, the following components are included based on part by weight,

| Pear juice | 5 to 15 parts |
|---|---|
| Greenish lily bulb juice | 0.5 to 5 parts |
| Fig juice | 0.5 to 5 parts |
| Water chestnut juice | 0.5 to 5 parts |
| Grosvenor momordica fruit extract | 0.05 to 0.1 parts |
| Grosvenor momordica fruit | 0.5 to 5 parts |
| Southern almond | 0.5 to 5 parts |
| Northern almond | 0.5 to 5 parts |
| Crystal sugar | 5 to 10 parts |
| Honey | 5 to 10 parts |

The present invention also provides a method for preparing the traditional Chinese medicine composition comprising the steps of:

The grosvenor momordica fruit, the southern almond and the northern almond are mixed and extracted with water to obtain an extract;

The crystal sugar, the honey, the pear juice, the greenish lily bulb juice, the fig juice, the water chestnut juice, the grosvenor momordica fruit extract and the extract described above are mixed to obtain the traditional Chinese medicine composition.

Preferably, the following components are included based on part By weight,

| Pear juice | 5 to 15 parts |
|---|---|
| Apple juice | 25 to 35 parts |
| Greenish lily bulb juice | 0.5 to 5 parts |
| Fig juice | 0.5 to 5 parts |
| Water chestnut juice | 0.5 to 5 parts |
| Grosvenor momordica fruit extract | 0.05 to 0.1 parts |
| Grosvenor momordica fruit | 0.5 to 5 parts |
| Southern almond | 0.5 to 5 parts |
| Northern almond | 0.5 to 5 parts |
| Honey | 5 to 10 parts |

The present invention also provides a method for preparing the traditional Chinese medicine composition comprising the steps of:

The grosvenor momordica fruit, the southern almond and the northern almond are mixed and extracted with water to obtain an extract;

The honey, the apple juice, the pear juice, the greenish lily bulb juice, the fig juice, the water chestnut juice, the grosvenor momordica fruit extract and the extract described above are mixed to obtain the traditional Chinese medicine composition.

Preferably, the following components are included based on part by weight,

| Pear juice | 5 to 15 parts |
|---|---|
| Apple juice | 25 to 35 parts |
| Greenish lily bulb juice | 0.5 to 5 parts |
| Fig juice | 0.5 to 5 parts |
| Water chestnut juice | 0.5 to 5 parts |
| Grosvenor momordica fruit extract | 0.05 to 0.1 parts |
| Grosvenor momordica fruit | 0.5 to 5 parts |
| Southern almond | 0.5 to 5 parts |
| Northern almond | 0.5 to 5 parts |
| Crystal sugar | 5 to 10 parts |
| Honey | 5 to 10 parts |

The present invention also provides a method for preparing the traditional Chinese medicine composition comprising the steps of:

The grosvenor momordica fruit, the southern almond and the northern almond are mixed and extracted with water to obtain an extract;

The crystal sugar, the honey, the apple juice, the pear juice, the greenish lily bulb juice, the fig juice, the water chestnut juice, the grosvenor momordica fruit extract and the extract described above are mixed to obtain the traditional Chinese medicine composition.

In the present invention, a traditional Chinese medicine composition is prepared without the addition of flavors, fragrances, artificial sweeteners and pigments, using pear juice, greenish lily bulb juice, fig juice, water chestnut juice, grosvenor momordica fruit, southern almond and northern almond as the main ingredients and one or the mixture of two or more of apple juice, crystal sugar and honey as the special additives based on the traditional Chinese medicine theory by adding choice medicinal and edible traditional Chinese medicine and natural and healthy food ingredients through scientific formulation design, and the obtained traditional Chinese medicine compositions of the present invention with a high content of juice have the effects of clearing heat and moistening the lungs.

In some embodiments provided in the present invention, there are 5 parts of pear juice, 28 parts of apple juice, 3 parts of greenish lily bulb juice, 5 parts of fig juice, 0.5 parts of water chestnut juice, 0.06 parts of grosvenor momordica fruit extract, 3 parts of grosvenor momordica fruit, 5 parts of southern almond, 0.5 parts of northern almond, 7 parts of crystal sugar and 9 parts of honey based on part by weight.

In further embodiments provided in the present invention, there are 10 parts of pear juice, 30 parts of apple juice, 5 parts of greenish lily bulb juice, 0.5 parts of fig juice, 1 part of water chestnut juice, 0.08 parts of grosvenor momordica fruit extract, 5 parts of grosvenor momordica fruit, 0.5 parts of southern almond, 1 part of northern almond, 9 parts of crystal sugar and 10 parts of honey based on part by weight.

In further embodiments provided in the present invention, there are 12 parts of pear juice, 35 parts of apple juice, 0.5 parts of greenish lily bulb juice, 1 part of fig juice, 3 parts of water chestnut juice, 0.1 parts of grosvenor momordica fruit extract, 0.5 parts of grosvenor momordica fruit, 1 part of southern almond, 3 parts of northern almond, 10 parts of crystal sugar and 5 parts of honey based on part by weight.

In further embodiments provided in the present invention, there are 15 parts of pear juice, 25 parts of apple juice, 1 part of greenish lily bulb juice, 3 parts of fig juice, 5 parts of water chestnut juice, 0.05 parts of grosvenor momordica fruit extract, 1 part of grosvenor momordica fruit, 3 parts of southern almond, 5 parts of northern almond, 5 parts of crystal sugar and 7 parts of honey based on part by weight.

The present invention also provides a method for preparing the traditional Chinese medicine composition comprising the steps of:

The grosvenor momordica fruit, the southern almond and the northern almond are mixed and extracted with water to obtain an extract;

The crystal sugar, the honey, the apple juice, the pear juice, the greenish lily bulb juice, the fig juice, the water chestnut juice and the extract described above are mixed to obtain the traditional Chinese medicine composition.

In some examples provided in the present invention, the extraction with water specifically includes: addition of 10 to 15 times of water, extraction at 90 to 100° C. for 2 to 3 hours, and repeated extractions for 2 or 3 times.

The present invention also provides use of the traditional Chinese medicine composition in the preparation of drugs or health food having the effects of clearing heat and moistening the lungs.

The present invention also provides a juice beverage comprising the traditional Chinese medicine composition provided in the present invention.

The present invention provides a traditional Chinese medicine composition, preparation methods and uses thereof The traditional Chinese medicine composition comprises the following ingredients: pear juice, greenish lily bulb juice, fig juice, water chestnut juice, grosvenor momordica fruit and/or grosvenor momordica fruit extract, southern almond and northern almond. The present invention has at least one of the following advantages:

The experimental results with respect to its effects indicate: The obtained composition of the present invention may significantly improve the phlegm-reducing effect of the rats (28% to 35%) and may significantly improve the cough-relieving effect of the rats (40% to 45%). The obtained composition of the present invention may significantly increase the total numbers of cells of the rats (26% to 30%), may significantly increase the numbers of macrophages of the rats (31% to 40%), may significantly reduce the numbers of lymphocytes of the rats (−55% to −48%), and may significantly reduce IL-6 (−37% to −30%), sIgA (−150% to −133%), IgG (−40% to −32%) and TNP-α (−30% to −24%) of bronchoalveolar lavage fluid of the rats, with a clearly better effects than those of Control A and Control B. As can be seen, the obtained composition of the present invention has significant promotions on the phlegm-reducing and cough-relieving capabilities of the rats, and has significant promotions on the immune indices of bronchoalveolar lavage fluid of the rats, exhibiting that the traditional Chinese medicine composition of the present invention has good effects of clearing heat and moistening the lungs.

Choice traditional Chinese medicines and food ingredients, that is, pear juice, apple juice, greenish lily bulb juice, fig juice, water chestnut juice, grosvenor momordica fruit, southern almond, northern almond, crystal sugar and honey are employed in the present invention without the addition of flavors and fragrances, artificial sweeteners and pigments, resulting in a high juice content, abundant nutrition and unique taste.

DETAILED DESCRIPTION

The present invention discloses a traditional Chinese medicine composition and the use thereof, which may be implemented with suitable modifications of the process parameters by those skilled in the art in light of the present disclosure. It is of particular note that all the similar alterations and modifications are clear to those skilled in the art and deemed to be included in the present invention. Methods and uses of the present invention have been described by the preferred examples, and it is obvious that those in related art are able to make changes or appropriate alternations and the combinations thereof to the methods and uses described herein to implement and apply the inventive technology without departing from the disclosure, spirit and scope of the present invention.

The ingredients or auxiliaries used in the traditional Chinese medicine composition and the uses thereof in the present invention are all commercially available. Among them, the apple juice, the pear juice, the greenish lily bulb juice and the fig juice are all concentrated fruit juice, wherein the apple juice has a soluble solids content of 69%, the pear juice has a soluble solids content of 69%, the greenish lily bulb juice has a soluble solids content of 19% and the fig juice has a soluble solids content of 38%; the water chestnut juice is original juice, with a soluble solids content of 6%. The grosvenor momordica fruit extract is a product on the market for sale.

The present invention is further explained in combination with the examples below.

EXAMPLE 1

The Preparation of the Traditional Chinese Medicine Composition

Extraction: 3 g grosvenor momordica fruit, 5 g southern almond and 0.5 g northern almond were weighed in proportion according to the formulation, and these materials were put into an extraction tank, then after the addition of 10 times of water the extraction was performed at 92° C. for 3 hours and repeated twice to obtain an extract, which was concentrated into a concentrate with a soluble solids content of 10-20%.

Formulation: the ingredients were weighed in proportion according to the formulation, and to the formulation tank were added: 33.94 g water, 7 g crystal sugar, 9 g honey, 28 g apple juice, 5 g pear juice, 3 g greenish lily bulb juice, 5 g fig juice, 0.5 g water chestnut juice, 0.06 g grosvenor momordica fruit extract and the concentrate described above. After the intermediates were stirred continuously for 10-15 min, the stirring was stopped and a sample was removed for tests, and after passing the tests, the traditional Chinese medicine composition was obtained.

EXAMPLE 2

The Preparation of the Traditional Chinese Medicine Composition

Extraction: 5 g grosvenor momordica fruit, 0.5 g southern almond and 1 g northern almond were weighed in proportion according to the formulation, and these materials were put into an extraction tank, then after the addition of 12 times of water the extraction was performed at 95° C. for 2 hours and repeated twice to obtain an extract, which was concentrated into a concentrate with a soluble solids content of 10-20%.

Formulation: the ingredients were weighed in proportion according to the formulation, and to the formulation tank were added: 27.92 g water, 9 g crystal sugar, 10 g honey, 30 g apple juice, 10 g pear juice, 5 g greenish lily bulb juice, 0.5 g fig juice, 1 g water chestnut juice, 0.08 g grosvenor momordica fruit extract and the concentrate described above. After the intermediates were stirred continuously for 10-15 min, the stirring was stopped and a sample was removed for tests, and after passing the tests, the traditional Chinese medicine composition was obtained.

EXAMPLE 3

The Preparation of the Traditional Chinese Medicine Composition

Extraction: 0.5 g grosvenor momordica fruit, 1 g southern almond and 3g northern almond were weighed in proportion according to the formulation, and these materials were put into an extraction tank, then after the addition of 14 times of water the extraction was performed at 100° C. for 3 hours and repeated three times to obtain an extract, which was concentrated into a concentrate with a soluble solids content of 10-20%.

Formulation: the ingredients were weighed in proportion according to the formulation, and to the formulation tank were added: 28.9 g water, 10 g crystal sugar, 5 g honey, 35 g apple juice, 12 g pear juice, 0.5 g greenish lily bulb juice, 1 g fig juice, 3 g water chestnut juice, 0.1 g grosvenor momordica fruit extract and the concentrate described above. After the intermediates were stirred continuously for 10-15 min, the stirring was stopped and a sample was removed for tests, and after passing the tests, the traditional Chinese medicine composition was obtained.

EXAMPLE 4

The Preparation of the Traditional Chinese Medicine Composition

Extraction: 1 g grosvenor momordica fruit, 3 g southern almond and 5 g northern almond were weighed in proportion according to the formulation, and these materials were put into an extraction tank, then after the addition of 15 times of water the extraction was performed at 90° C. for 2 hours and repeated three times to obtain an extract, which was concentrated into a concentrate with a soluble solids content of 10-20%.

Formulation: the ingredients were weighed in proportion according to the formulation, and to the formulation tank were added: 29.95 g water, 5 g crystal sugar, 7 g honey, 25 g apple juice, 15 g pear juice, 1 g greenish lily bulb juice, 3 g fig juice, 5 g water chestnut juice, 0.05 g grosvenor momordica fruit extract and the concentrate described above. After the intermediates were stirred continuously for 10-15 min, the stirring was stopped and a sample was removed for tests, and after passing the tests, the traditional Chinese medicine composition was obtained.

EXAMPLE 5

The Preparation of the Traditional Chinese Medicine Composition

Extraction: 3 g grosvenor momordica fruit, 5 g southern almond and 0.5 g northern almond were weighed in proportion according to the formulation, and these materials were put into an extraction tank, then after the addition of 10 times of water the extraction was performed at 92° C. for 3 hours and repeated twice to obtain an extract, which was concentrated into a concentrate with a soluble solids content of 10-20%.

Formulation: the ingredients were weighed in proportion according to the formulation, and to the formulation tank were added: 33.94 g water, 5 g pear juice, 3 g greenish lily bulb juice, 5 g fig juice, 0.5g water chestnut juice, 0.06 g grosvenor momordica fruit extract and the concentrate described above. After the intermediates were stirred continuously for 10-15 min, the stirring was stopped and a sample was removed for tests, and after passing the tests, the traditional Chinese medicine composition was obtained.

EXAMPLE 6

The Preparation of the Traditional Chinese Medicine Composition

Extraction: 5 g grosvenor momordica fruit, 0.5 g southern almond and 1 g northern almond were weighed in proportion according to the formulation, and these materials were put into an extraction tank, then after the addition of 12 times of water the extraction was performed at 95° C. for 2 hours and repeated twice to obtain an extract, which was concentrated into a concentrate with a soluble solids content of 10-20%.

Formulation: the ingredients were weighed in proportion according to the formulation, and to the formulation tank were added: 27.92 g water, 10 g pear juice, 5 g greenish lily bulb juice, 0.5 g fig juice, 1 g water chestnut juice, 0.08 g grosvenor momordica fruit extract and the concentrate described above. After the intermediates were stirred continuously for 10-15 min, the stirring was stopped and a sample was removed for tests, and after passing the tests, the traditional Chinese medicine composition was obtained.

EXAMPLE 7

The Preparation of the Traditional Chinese Medicine Composition

Extraction: 0.5 g grosvenor momordica fruit, 1 g southern almond and 3g northern almond were weighed in proportion according to the formulation, and these materials were put into an extraction tank, then after the addition of 14 times of water the extraction was performed at 100° C. for 3 hours and repeated three times to obtain an extract, which was concentrated into a concentrate with a soluble solids content of 10-20%.

Formulation: the ingredients were weighed in proportion according to the formulation, and to the formulation tank were added: 28.9 g water, 12 g pear juice, 0.5 g greenish lily bulb juice, 1 g fig juice, 3 g water chestnut juice, 0.1 g grosvenor momordica fruit extract and the concentrate described above. After the intermediates were stirred continuously for 10-15 min, the stirring was stopped and a sample was removed for tests, and after passing the tests, the traditional Chinese medicine composition was obtained.

EXAMPLE 8

The Preparation of the Traditional Chinese Medicine Composition

Extraction: 1 g grosvenor momordica fruit, 3 g southern almond and 5 g northern almond were weighed in proportion according to the formulation, and these materials were put into an extraction tank, then after the addition of 15 times of water the extraction was performed at 90° C. for 2 hours and repeated three times to obtain an extract, which was concentrated into a concentrate with a soluble solids content of 10-20%.

Formulation: the ingredients were weighed in proportion according to the formulation, and to the formulation tank were added: 29.95 g water, 15 g pear juice, 1 g greenish lily bulb juice, 3 g fig juice, 5 g water chestnut juice, 0.05 g grosvenor momordica fruit extract and the concentrate described above. After the intermediates were stirred continuously for 10-15 min, the stirring was stopped and a sample was removed for tests, and after passing the tests, the traditional Chinese medicine composition was obtained.

EXAMPLE 9

The Preparation of the Traditional Chinese Medicine Composition

Extraction: 3 g grosvenor momordica fruit, 5 g southern almond and 0.5 g northern almond were weighed in proportion according to the formulation, and these materials were put into an extraction tank, then after the addition of 10 times of water the extraction was performed at 92° C. for 3 hours and repeated twice to obtain an extract, which was concentrated into a concentrate with a soluble solids content of 10-20%.

Formulation: the ingredients were weighed in proportion according to the formulation, and to the formulation tank were added: 33.94 g water, 28 g apple juice, 5 g pear juice, 3 g greenish lily bulb juice, 5 g fig juice, 0.5 g water chestnut juice, 0.06 g grosvenor momordica fruit extract and the concentrate described above. After the intermediates were stirred continuously for 10-15 min, the stirring was stopped and a sample was removed for tests, and after passing the tests, the traditional Chinese medicine composition was obtained.

EXAMPLE 10

The Preparation of the Traditional Chinese Medicine Composition

Extraction: 5 g grosvenor momordica fruit, 0.5 g southern almond and 1 g northern almond were weighed in proportion according to the formulation, and these materials were put into an extraction tank, then after the addition of 12 times of water the extraction was performed at 95° C. for 2 hours and repeated twice to obtain an extract, which was concentrated into a concentrate with a soluble solids content of 10-20%.

Formulation: the ingredients were weighed in proportion according to the formulation, and to the formulation tank were added: 27.92g water, 30 g apple juice, 10 g pear juice, 5 g greenish lily bulb juice, 0.5g fig juice, 1 g water chestnut juice, 0.08 g grosvenor momordica fruit extract and the concentrate described above. After the intermediates were stirred continuously for 10-15 min, the stirring was stopped and a sample was removed for tests, and after passing the tests, the traditional Chinese medicine composition was obtained.

EXAMPLE 11

The Preparation of the Traditional Chinese Medicine Composition

Extraction: 0.5 g grosvenor momordica fruit, 1 g southern almond and 3 g northern almond were weighed in proportion according to the formulation, and these materials were put into an extraction tank, then after the addition of 14 times of water the extraction was performed at 100° C. for 3 hours and repeated three times to obtain an extract, which was concentrated into a concentrate with a soluble solids content of 10-20%.

Formulation: the ingredients were weighed in proportion according to the formulation, and to the formulation tank were added: 28.9 g water, 35 g apple juice, 12 g pear juice, 0.5 g greenish lily bulb juice, 1 g fig juice, 3 g water chestnut juice, 0.1 g grosvenor momordica fruit extract and the concentrate described above. After the intermediates were stirred continuously for 10-15 min, the stirring was stopped and a sample was removed for tests, and after passing the tests, the traditional Chinese medicine composition was obtained.

EXAMPLE 12

The Preparation of the Traditional Chinese Medicine Composition

Extraction: 1 g grosvenor momordica fruit, 3 g southern almond and 5 g northern almond were weighed in proportion according to the formulation, and these materials were put into an extraction tank, then after the addition of 15 times of water the extraction was performed at 90° C. for 2 hours and repeated three times to obtain an extract, which was concentrated into a concentrate with a soluble solids content of 10-20%.

Formulation: the ingredients were weighed in proportion according to the formulation, and to the formulation tank were added: 29.95 g water, 25 g apple juice, 15 g pear juice, 1 g greenish lily bulb juice, 3 g fig juice, 5 g water chestnut juice, 0.05 g grosvenor momordica fruit extract and the concentrate described above. After the intermediates were stirred continuously for 10-15 min, the stirring was stopped and a sample was removed for tests, and after passing the tests, the traditional Chinese medicine composition was obtained.

EXAMPLE 13

The Preparation of the Traditional Chinese Medicine Composition

Extraction: 3 g grosvenor momordica fruit, 5 g southern almond and 0.5 g northern almond were weighed in proportion according to the formulation, and these materials were put into an extraction tank, then after the addition of 10 times of water the extraction was performed at 92° C. for 3 hours and repeated twice to obtain an extract, which was concentrated into a concentrate with a soluble solids content of 10-20%.

Formulation: the ingredients were weighed in proportion according to the formulation, and to the formulation tank were added: 33.94 g water, 7 g crystal sugar, 5 g pear juice, 3 g greenish lily bulb juice, 5 g fig juice, 0.5 g water chestnut juice, 0.06 g grosvenor momordica fruit extract and the concentrate described above. After the intermediates were stirred continuously for 10-15 min, the stirring was stopped and a sample was removed for tests, and after passing the tests, the traditional Chinese medicine composition was obtained.

EXAMPLE 14

The Preparation of the Traditional Chinese Medicine Composition

Extraction: 5 g grosvenor momordica fruit, 0.5 g southern almond and 1 g northern almond were weighed in proportion according to the formulation, and these materials were put into an extraction tank, then after the addition of 12 times of water the extraction was performed at 95° C. for 2 hours and repeated twice to obtain an extract, which was concentrated into a concentrate with a soluble solids content of 10-20%.

Formulation: the ingredients were weighed in proportion according to the formulation, and to the formulation tank were added: 27.92 g water, 9 g crystal sugar, 10 g pear juice, 5 g greenish lily bulb juice, 0.5 g fig juice, 1 g water chestnut juice, 0.08 g grosvenor momordica fruit extract and the concentrate described above. After the intermediates were stirred continuously for 10-15min, the stirring was stopped and a sample was removed for tests, and after passing the tests, the traditional Chinese medicine composition was obtained.

EXAMPLE 15

The Preparation of the Traditional Chinese Medicine Composition

Extraction: 0.5 g grosvenor momordica fruit, 1 g southern almond and 3g northern almond were weighed in proportion according to the formulation, and these materials were put into an extraction tank, then after the addition of 14 times of water the extraction was performed at 100° C. for 3 hours and repeated three times to obtain an extract, which was concentrated into a concentrate with a soluble solids content of 10-20%.

Formulation: the ingredients were weighed in proportion according to the formulation, and to the formulation tank were added: 28.9 g water, 10 g crystal sugar, 12 g pear juice, 0.5 g greenish lily bulb juice, 1 g fig juice, 3g water chestnut juice, 0.1 g grosvenor momordica fruit extract and the concentrate described above. After the intermediates were stirred continuously for 10-15 min, the stirring was stopped and a sample was removed for tests, and after passing the tests, the traditional Chinese medicine composition was obtained.

EXAMPLE 16

The Preparation of the Traditional Chinese Medicine Composition

Extraction: 1 g grosvenor momordica fruit, 3 g southern almond and 5 g northern almond were weighed in proportion according to the formulation, and these materials were put into an extraction tank, then after the addition of 15 times of water the extraction was performed at 90° C. for 2 hours and repeated three times to obtain an extract, which was concentrated into a concentrate with a soluble solids content of 10-20%.

Formulation: the ingredients were weighed in proportion according to the formulation, and to the formulation tank were added: 29.95 g water, 5 g crystal sugar, 15 g pear juice, 1 g greenish lily bulb juice, 3 g fig juice, 5 g water chestnut juice, 0.05 g grosvenor momordica fruit extract and the concentrate described above. After the intermediates were stirred continuously for 10-15 min, the stirring was stopped and a sample was removed for tests, and after passing the tests, the traditional Chinese medicine composition was obtained.

EXAMPLE 17

The Preparation of the Traditional Chinese Medicine Composition

Extraction: 3 g grosvenor momordica fruit, 5 g southern almond and 0.5 g northern almond were weighed in proportion according to the formulation, and these materials were put into an extraction tank, then after the addition of 10 times of water the extraction was performed at 92° C. for 3 hours and repeated twice to obtain an extract, which was concentrated into a concentrate with a soluble solids content of 10-20%.

Formulation: the ingredients were weighed in proportion according to the formulation, and to the formulation tank were added: 33.94 g water, 7 g crystal sugar, 28 g apple juice, 5 g pear juice, 3 g greenish lily bulb juice, 5 g fig juice, 0.5 g water chestnut juice, 0.06 g grosvenor momordica fruit extract and the concentrate described above. After the intermediates were stirred continuously for 10-15 min, the stirring was stopped and a sample was removed for tests, and after passing the tests, the traditional Chinese medicine composition was obtained.

EXAMPLE 18

The Preparation of the Traditional Chinese Medicine Composition

Extraction: 5 g grosvenor momordica fruit, 0.5 g southern almond and 1 g northern almond were weighed in proportion according to the formulation, and these materials were put into an extraction tank, then after the addition of 12 times of water the extraction was performed at 95° C. for 2 hours and repeated twice to obtain an extract, which was concentrated into a concentrate with a soluble solids content of 10-20%.

Formulation: the ingredients were weighed in proportion according to the formulation, and to the formulation tank were added: 27.92 g water, 9 g crystal sugar, 30 g apple juice, 10 g pear juice, 5 g greenish lily bulb juice, 0.5 g fig juice, 1 g water chestnut juice, 0.08 g grosvenor momordica fruit extract and the concentrate described above. After the intermediates were stirred continuously for 10-15 min, the stirring was stopped and a sample was removed for tests, and after passing the tests, the traditional Chinese medicine composition was obtained.

EXAMPLE 19

The Preparation of the Traditional Chinese Medicine Composition

Extraction: 0.5 g grosvenor momordica fruit, 1 g southern almond and 3 g northern almond were weighed in proportion according to the formulation, and these materials were put into an extraction tank, then after the addition of 14 times of water the extraction was performed at 100° C. for 3 hours and repeated three times to obtain an extract, which was concentrated into a concentrate with a soluble solids content of 10-20%.

Formulation: the ingredients were weighed in proportion according to the formulation, and to the formulation tank were added: 28.9 g water, 10 g crystal sugar, 35 g apple juice, 12 g pear juice, 0.5 g greenish lily bulb juice, 1 g fig juice, 3 g water chestnut juice, 0.1 g grosvenor momordica fruit extract and the concentrate described above. After the intermediates were stirred continuously for 10-15 min, the stirring was stopped and a sample was removed for tests, and after passing the tests, the traditional Chinese medicine composition was obtained.

EXAMPLE 20

The Preparation of the Traditional Chinese Medicine Composition

Extraction: 1 g grosvenor momordica fruit, 3 g southern almond and 5 g northern almond were weighed in proportion according to the formulation, and these materials were put into an extraction tank, then after the addition of 15 times of water the extraction was performed at 90° C. for 2 hours and repeated three times to obtain an extract, which was concentrated into a concentrate with a soluble solids content of 10-20%.

Formulation: the ingredients were weighed in proportion according to the formulation, and to the formulation tank were added: 29.95 g water, 5 g crystal sugar, 25 g apple juice, 15 g pear juice, 1 g greenish lily bulb juice, 3 g fig juice, 5 g water chestnut juice, 0.05 g grosvenor momordica fruit extract and the concentrate described above. After the intermediates were stirred continuously for 10-15 min, the stirring was stopped and a sample was removed for tests, and after passing the tests, the traditional Chinese medicine composition was obtained.

EXAMPLE 21

The Preparation of the Traditional Chinese Medicine Composition

Extraction: 3 g grosvenor momordica fruit, 5 g southern almond and 0.5 g northern almond were weighed in proportion according to the formulation, and these materials were put into an extraction tank, then after the addition of 10 times of water the extraction was performed at 92° C. for 3 hours and repeated twice to obtain an extract, which was concentrated into a concentrate with a soluble solids content of 10-20%.

Formulation: the ingredients were weighed in proportion according to the formulation, and to the formulation tank were added: 33.94 g water, 9 g honey, 5 g pear juice, 3 g greenish lily bulb juice, 5 g fig juice, 0.5 g water chestnut juice, 0.06 g grosvenor momordica fruit extract and the concentrate described above. After the intermediates were stirred continuously for 10-15 min, the stirring was stopped and a sample was removed for tests, and after passing the tests, the traditional Chinese medicine composition was obtained.

EXAMPLE 22

The Preparation of the Traditional Chinese Medicine Composition

Extraction: 5 g grosvenor momordica fruit, 0.5 g southern almond and 1 g northern almond were weighed in proportion according to the formulation, and these materials were put into an extraction tank, then after the addition of 12 times of water the extraction was performed at 95° C. for 2 hours and repeated twice to obtain an extract, which was concentrated into a concentrate with a soluble solids content of 10-20%.

Formulation: the ingredients were weighed in proportion according to the formulation, and to the formulation tank were added: 27.92 g water, 10 g honey, 10 g pear juice, 5 g greenish lily bulb juice, 0.5 g fig juice, 1 g water chestnut juice, 0.08 g grosvenor momordica fruit extract and the concentrate described above. After the intermediates were stirred continuously for 10-15 min, the stirring was stopped and a sample was removed for tests, and after passing the tests, the traditional Chinese medicine composition was obtained.

EXAMPLE 23

The Preparation of the Traditional Chinese Medicine Composition

Extraction: 0.5 g grosvenor momordica fruit, 1 g southern almond and 3 g northern almond were weighed in proportion according to the formulation, and these materials were put into an extraction tank, then after the addition of 14 times of water the extraction was performed at 100° C. for 3 hours and repeated three times to obtain an extract, which was concentrated into a concentrate with a soluble solids content of 10-20%.

Formulation: the ingredients were weighed in proportion according to the formulation, and to the formulation tank were added: 28.9 g water, 5 g honey, 12 g pear juice, 0.5 g greenish lily bulb juice, 1 g fig juice, 3 g water chestnut juice, 0.1 g grosvenor momordica fruit extract and the concentrate described above. After the intermediates were stirred continuously for 10-15 min, the stirring was stopped and a sample was removed for tests, and after passing the tests, the traditional Chinese medicine composition was obtained.

EXAMPLE 24

The Preparation of the Traditional Chinese Medicine Composition

Extraction: 1 g grosvenor momordica fruit, 3 g southern almond and 5 g northern almond were weighed in proportion according to the formulation, and these materials were put into an extraction tank, then after the addition of 15 times of water the extraction was performed at 90° C. for 2 hours and repeated three times to obtain an extract, which was concentrated into a concentrate with a soluble solids content of 10-20%.

Formulation: the ingredients were weighed in proportion according to the formulation, and to the formulation tank were added: 29.95 g water, 7 g honey, 15 g pear juice, 1 g greenish lily bulb juice, 3 g fig juice, 5 g water chestnut juice, 0.05 g grosvenor momordica fruit extract and the concentrate described above. After the intermediates were stirred continuously for 10-15 min, the stirring was stopped and a sample was removed for tests, and after passing the tests, the traditional Chinese medicine composition was obtained.

EXAMPLE 25

The Preparation of the Traditional Chinese Medicine Composition

Extraction: 3 g grosvenor momordica fruit, 5 g southern almond and 0.5 g northern almond were weighed in proportion according to the formulation, and these materials were put into an extraction tank, then after the addition of 10 times of water the extraction was performed at 92° C. for 3 hours and repeated twice to obtain an extract, which was concentrated into a concentrate with a soluble solids content of 10-20%.

Formulation: the ingredients were weighed in proportion according to the formulation, and to the formulation tank were added: 33.94 g water, 7 g crystal sugar, 9 g honey, 5 g pear juice, 3 g greenish lily bulb juice, 5 g fig juice, 0.5 g water chestnut juice, 0.06 g grosvenor momordica fruit extract and the concentrate described above. After the intermediates were stirred continuously for 10-15 min, the stirring was stopped and a sample was removed for tests, and after passing the tests, the traditional Chinese medicine composition was obtained.

EXAMPLE 26

The Preparation of the Traditional Chinese Medicine Composition

Extraction: 5 g grosvenor momordica fruit, 0.5 g southern almond and 1 g northern almond were weighed in proportion according to the formulation, and these materials were put into an extraction tank, then after the addition of 12 times of water the extraction was performed at 95° C. for 2 hours and repeated twice to obtain an extract, which was concentrated into a concentrate with a soluble solids content of 10-20%.

Formulation: the ingredients were weighed in proportion according to the formulation, and to the formulation tank were added: 27.92 g water, 9 g crystal sugar, 10 g honey, 10 g pear juice, 5 g greenish lily bulb juice, 0.5 g fig juice, 1 g water chestnut juice, 0.08 g grosvenor momordica fruit extract and the concentrate described above. After the intermediates were stirred continuously for 10-15 min, the stirring was stopped and a sample was removed for tests, and after passing the tests, the traditional Chinese medicine composition was obtained.

EXAMPLE 27

The Preparation Of The Traditional Chinese Medicine Composition

Extraction: 0.5 g grosvenor momordica fruit, 1 g southern almond and 3 g northern almond were weighed in proportion according to the formulation, and these materials were put into an extraction tank, then after the addition of 14 times of water the extraction was performed at 100° C. for 3 hours and repeated three times to obtain an extract, which was concentrated into a concentrate with a soluble solids content of 10-20%.

Formulation: the ingredients were weighed in proportion according to the formulation, and to the formulation tank were added: 28.9 g water, 10 g crystal sugar, 5 g honey, 12 g pear juice, 0.5 g greenish lily bulb juice, 1 g fig juice, 3 g water chestnut juice, 0.1 g grosvenor momordica fruit extract and the concentrate described above. After the intermediates were stirred continuously for 10-15 min, the stirring was stopped and a sample was removed for tests, and after passing the tests, the traditional Chinese medicine composition was obtained.

EXAMPLE 28

The Preparation of the Traditional Chinese Medicine Composition

Extraction: 1 g grosvenor momordica fruit, 3 g southern almond and 5 g northern almond were weighed in proportion according to the formulation, and these materials were put into an extraction tank, then after the addition of 15 times of water the extraction was performed at 90° C. for 2 hours and repeated three times to obtain an extract, which was concentrated into a concentrate with a soluble solids content of 10-20%.

Formulation: the ingredients were weighed in proportion according to the formulation, and to the formulation tank were added: 29.95 g water, 5 g crystal sugar, 7 g honey, 15 g pear juice, 1 g greenish lily bulb juice, 3 g fig juice, 5 g water chestnut juice, 0.05 g grosvenor momordica fruit extract and the concentrate described above. After the intermediates were stirred continuously for 10-15 min, the stirring was stopped and a sample was removed for tests, and after passing the tests, the traditional Chinese medicine composition was obtained.

EXAMPLE 29

The Preparation of the Traditional Chinese Medicine Composition

Extraction: 3 g grosvenor momordica fruit, 5 g southern almond and 0.5 g northern almond were weighed in proportion according to the formulation, and these materials were put into an extraction tank, then after the addition of 10 times of water the extraction was performed at 92° C. for 3 hours and repeated twice to obtain an extract, which was concentrated into a concentrate with a soluble solids content of 10-20%.

Formulation: the ingredients were weighed in proportion according to the formulation, and to the formulation tank were added: 33.94 g water, 9 g honey, 28 g apple juice, 5 g pear juice, 3 g greenish lily bulb juice, 5 g fig juice, 0.5 g water chestnut juice, 0.06 g grosvenor momordica fruit extract and the concentrate described above. After the intermediates were stirred continuously for 10-15 min, the stirring was stopped and a sample was removed for tests, and after passing the tests, the traditional Chinese medicine composition was obtained.

EXAMPLE 30

The Preparation of the Traditional Chinese Medicine Composition

Extraction: 5 g grosvenor momordica fruit, 0.5 g southern almond and 1 g northern almond were weighed in proportion according to the formulation, and these materials were put into an extraction tank, then after the addition of 12 times of water the extraction was performed at 95° C. for 2 hours and repeated twice to obtain an extract, which was concentrated into a concentrate with a soluble solids content of 10-20%.

Formulation: the ingredients were weighed in proportion according to the formulation, and to the formulation tank were added: 27.92 g water, 10 g honey, 30 g apple juice, 10 g pear juice, 5 g greenish lily bulb juice, 0.5 g fig juice, 1 g water chestnut juice, 0.08 g grosvenor momordica fruit extract and the concentrate described above. After the intermediates were stirred continuously for 10-15 min, the stirring was stopped and a sample was removed for tests, and after passing the tests, the traditional Chinese medicine composition was obtained.

EXAMPLE 31

The Preparation of the Traditional Chinese Medicine Composition

Extraction: 0.5 g grosvenor momordica fruit, 1 g southern almond and 3 g northern almond were weighed in proportion according to the formulation, and these materials were put into an extraction tank, then after the addition of 14 times of water the extraction was performed at 100° C. for 3 hours and repeated three times to obtain an extract, which was concentrated into a concentrate with a soluble solids content of 10-20%.

Formulation: the ingredients were weighed in proportion according to the formulation, and to the formulation tank were added: 28.9 g water, 5 g honey, 35 g apple juice, 12 g pear juice, 0.5 g greenish lily bulb juice, 1 g fig juice, 3 g water chestnut juice, 0.1 g grosvenor momordica fruit extract and the concentrate described above. After the intermediates were stirred continuously for 10-15 min, the stirring was stopped and a sample was removed for tests, and after passing the tests, the traditional Chinese medicine composition was obtained.

EXAMPLE 32

The Preparation of the Traditional Chinese Medicine Composition

Extraction: 1 g grosvenor momordica fruit, 3 g southern almond and 5 g northern almond were weighed in proportion according to the formulation, and these materials were put into an extraction tank, then after the addition of 15 times of water the extraction was performed at 90° C. for 2 hours and repeated three times to obtain an extract, which was concentrated into a concentrate with a soluble solids content of 10-20%.

Formulation: the ingredients were weighed in proportion according to the formulation, and to the formulation tank were added: 29.95 g water, 7 g honey, 25 g apple juice, 15 g pear juice, 1 g greenish lily bulb juice, 3 g fig juice, 5 g water chestnut juice, 0.05 g grosvenor momordica fruit extract and the concentrate described above. After the intermediates were stirred continuously for 10-15 min, the stirring was stopped and a sample was removed for tests, and after passing the tests, the traditional Chinese medicine composition was obtained.

EXAMPLE 33

Tests of Effects

1 Experimental samples and methods
1.1 Experimental samples

The compositions obtained in Examples 1 to 8 of the present application were taken as the experimental samples, the composition in the Example of Publication No. CN 104041873 A as Control A, the composition disclosed in Publication No. CN 103461870 A as Control B, and pure water as Control C.

1.2 Experimental Objects

Adult rats were taken as experimental objects, and divided into 11 groups, that is, Example 1 to 8 groups, Control A group, Control B group and Control C group respectively to conduct the experiments, with an amount of 20 rats in each group.

The rats were irrigated using Example 1 to 8 groups, Control A, Control B and Control C 5 days a week for two weeks.

1.3 Experimental Methods

The amounts of phenol red secretion of the rats were measured through phenol red secretion experiments, and taking Control C as a reference, the experimental sample groups, Control A and Control B were compared with Control C to calculate the percentage of increases and decreases of the data in each group relative to that in Control C to evaluate the phlegm reducing effects of the tested samples.

The cough incubation and cough frequency of the rats were measured through cough-inducing experiments by sulfur dioxide, and the experimental sample groups, Control A and Control B were compared with Control C to evaluate the cough-reliving effects of the tested samples with reference to the evaluation method for the phlegm-reducing effects.

The changes of immune indices in the lungs of the rats were measured through the smoking experiments of the rats, and the experimental sample groups, Control A and Control B were compared with Control C to evaluate the immunity-enhancing effects of the tested samples with reference to the evaluation method for the phlegm-reducing effects.

2. Experimental Results

TABLE 1

The phlegm-reducing effects of the rats in different groups

| Group | Phlegm-reducing effects |
|---|---|
| Example 1 | 30% |
| Example 2 | 35% |
| Example 3 | 28% |
| Example 4 | 29% |
| Example 5 | 30% |
| Example 6 | 33% |
| Example 7 | 35% |
| Example 8 | 30% |
| Control A | 7% |
| Control B | 5% |
| Control C | — |

TABLE 2

The cough-relieving effects of the rats in different groups

| Group | Cough-relieving effects |
|---|---|
| Example 1 | 42% |
| Example 2 | 45% |
| Example 3 | 40% |
| Example 4 | 41% |
| Example 5 | 44% |
| Example 6 | 41% |
| Example 7 | 43% |
| Example 8 | 40% |
| Control A | 10% |
| Control B | 15% |
| Control C | — |

TABLE 3

The immune indices of bronchoalveolar lavage fluid of the rats in different groups (I)

| Group | Total number of cells | Number of macrophages | Number of lymphocytes |
|---|---|---|---|
| Example 1 | 28% | 36% | −52% |
| Example 2 | 30% | 40% | −48% |
| Example 3 | 27% | 33% | −55% |
| Example 4 | 26% | 31% | −50% |
| Example 5 | 29% | 37% | −53% |
| Example 6 | 28% | 39% | −55% |
| Example 7 | 30% | 40% | −50% |
| Example 8 | 29% | 34% | −54% |
| Control A | 7% | 8% | −12% |
| Control B | 6% | 8% | −10% |
| Control C | — | — | — |

TABLE 4

The immune indices of bronchoalveolar lavage fluid of the rats in different groups (II)

| Group | IL-6 | sIgA | IgG | Tnf-α |
|---|---|---|---|---|
| Example 1 | −30% | −133% | −33% | −27% |
| Example 2 | −33% | −150% | −36% | −30% |
| Example 3 | −37% | −142% | −40% | −25% |
| Example 4 | −34% | −140% | −32% | −24% |
| Example 5 | −32% | −145% | −35% | −29% |
| Example 6 | −33% | −150% | −40% | −28% |
| Example 7 | −36% | −144% | −39% | −30% |
| Example 8 | −35% | −140% | −37% | −28% |
| Control A | −5% | −10% | −6% | −4% |
| Control B | −3% | −8% | −5% | −5% |
| Control C | — | — | — | — |

As seen from Table 1, the compositions of Examples 1 to 8 of the present invention may significantly improve the phlegm-reducing effects (28% to 35%) of the rats, which are substantially higher than those of Control A (7%) and Control B (5%).

As seen from Table 2, the compositions of Examples 1 to 8 of the present invention may significantly improve the cough-relieving effects (40% to 45%) of the rats, which are substantially higher than those of Control A (10%) and Control B (15%).

As seen from Table 3, the compositions of Examples 1 to 8 of the present invention may significantly increase the total numbers of cells (26% to 30%) of the rats, which are substantially higher than those of Control A (7%) and Control B (6%); the compositions of Examples 1 to 8 of the present invention may significantly increase the numbers of macrophages (31% to 40%) of the rats, which are substantially higher than those of Control A (8%) and Control B (8%); the compositions of Examples 1 to 8 of the present invention may significantly reduce the numbers of lymphocytes (−55% to −48%) of the rats, and the proportion of decrease are substantially higher than those of Control A (−12%) and Control B (−10%);

As seen from Table 4, the compositions of Examples 1 to 8 of the present invention may significantly reduce IL-6 (−37% to −30%), sIgA (−150% to −133%), IgG (−40% to −32%) and TNP-α (−30% to −24%) of bronchoalveolar lavage fluid of the rats, which are substantially higher than those of Control A (IL-6: −5%, sIgA: −10%, IgG: −6%, TNF-α: −5%) and Control B (IL-6: −3%, sIgA: −8%, IgG: −5%, TNF-α: −5%).

A comprehensive analysis of the results above shows that the obtained compositions in Example 1 to 8 of the present invention have significant promotions on the phlegm-reducing and cough-relieving capabilities of the rats, which are superior to those of Control A and Control B; the obtained compositions in Example 1 to 8 of the present invention may significantly increase the total number of cells and the number of macrophages of the rats and may significantly reduce the increase of lymphocytes, IL-6, sIgA, IgG and TNF-αof the rats due to smoking, thus having a significant promotion on the immune indices of bronchoalveolar lavage fluid of the rats, which is superior to those of Control A and Control B.

In summary, the traditional Chinese medicine composition of the present invention has good effects of clearing heat and moistening the lungs.

EXAMPLE 34

The Preparation of the Juice Beverage

Homogenization: the traditional Chinese medicine composition obtained in Example 1 was taken and pre-heated to 60° C. before entering the homogenizer having a pressure of 30 Mpa.

Sterilization: The intermediates were sterilized using UHT sterilizer at a sterilizing temperature of 120° C. for a sterilizing time of 30 s.

Bottling: the bottling temperature is 65-75° C., and the bottling concentration is generally 45-55%.

Cooling: the concentrate after bottling was cooled by water spraying at normal temperature for 30 min, with a temperature after cooling ≤40° C.

Light examination and packaging were performed to obtain the juice beverage.

EXAMPLE 35

The Preparation of the Juice Beverage

Homogenization: the traditional Chinese medicine composition obtained in Example 2 was taken and pre-heated to 65° C. before entering the homogenizer having a pressure of 20 Mpa.

Sterilization: The intermediates were sterilized using UHT sterilizer at a sterilizing temperature of 130° C. for a sterilizing time of 10 s.

Bottling: the bottling temperature is 65-75° C., and the bottling concentration is generally 45-55%.

Cooling: the concentrate after bottling was cooled by water spraying at normal temperature for 30 min, with a temperature after cooling ≤40° C.

Light examination and packaging were performed to obtain the juice beverage.

EXAMPLE 36

The Preparation of the Juice Beverage

Homogenization: the traditional Chinese medicine composition obtained in Example 3 was taken and pre-heated to 70° C. before entering the homogenizer having a pressure of 15 Mpa.

Sterilization: The intermediates were sterilized using UHT sterilizer at a sterilizing temperature of 135° C. for a sterilizing time of 5 s.

Bottling: the bottling temperature is 65-75° C., and the bottling concentration is generally 45-55%.

Cooling: the concentrate after bottling was cooled by water spraying at normal temperature for 30 min, with a temperature after cooling ≤40° C. .

Light examination and packaging were performed to obtain the juice beverage.

The above description gives only the preferred embodiments of the present invention, and it should be noted that for those of ordinary skill in the art, a number of improvements and modifications can be made without departing from the principle of the invention, which are also regarded as falling into the scope claimed in the present invention.

The invention claimed is:

1. A composition for reducing phlem and relieving cough in a human in need thereof consisting essentially of the following components by weight,

| | |
|---|---|
| Pear juice | 5 to 15 parts; |
| Apple juice | 25 to 35 parts; |
| Greenish lily bulb juice | 0.5 to 5 parts; |
| Fig juice | 0.5 to 5 parts; |
| Water chestnut juice | 0.5 to 5 parts; |
| Grosvenor momordica fruit extract | 0.05 to 0.1 parts; |
| Grosvenor momordica fruit | 0.5 to 5 parts; |
| Southern almond | 0.5 to 5 parts; and |
| Northern almond | 0.5 to 5 parts. |

2. A composition for reducing phlem and relieving cough in a human in need thereof consisting essentially of the following components by weight,

| | |
|---|---|
| Pear juice | 5 to 15 parts; |
| Greenish lily bulb juice | 0.5 to 5 parts; |
| Fig juice | 0.5 to 5 parts; |
| Water chestnut juice | 0.5 to 5 parts; |
| Grosvenor momordica fruit extract | 0.05 to 0.1 parts; |
| Grosvenor momordica fruit | 0.5 to 5 parts; |
| Southern almond | 0.5 to 5 parts; |
| Northern almond | 0.5 to 5 parts; and |
| Crystal sugar | 5 to 10 parts. |

3. A composition for reducing phlem and relieving cough in a human in need thereof consisting essentially of the following components by weight,

| | |
|---|---|
| Pear juice | 5 to 15 parts; |
| Apple juice | 25 to 35 parts; |
| Greenish lily bulb juice | 0.5 to 5 parts; |
| Fig juice | 0.5 to 5 parts; |
| Water chestnut juice | 0.5 to 5 parts; |
| Grosvenor momordica fruit extract | 0.05 to 0.1 parts; |
| Grosvenor momordica fruit | 0.5 to 5 parts; |
| Southern almond | 0.5 to 5 parts; |
| Northern almond | 0.5 to 5 parts; and |
| Crystal sugar | 5 to 10 parts. |

4. A composition for reducing phlem and relieving cough in a human in need thereof consisting essentially of the following components by weight,

| | |
|---|---|
| Pear juice | 5 to 15 parts; |
| Greenish lily bulb juice | 0.5 to 5 parts; |
| Fig juice | 0.5 to 5 parts; |
| Water chestnut juice | 0.5 to 5 parts; |
| Grosvenor momordica fruit extract | 0.05 to 0.1 parts; |
| Grosvenor momordica fruit | 0.5 to 5 parts; |
| Southern almond | 0.5 to 5 parts; |
| Northern almond | 0.5 to 5 parts; and |
| Honey | 5 to 10 parts. |

5. A composition for reducing phlem and relieving cough in a human in need thereof consisting essentially of the following components by weight,

| | |
|---|---|
| Pear juice | 5 to 15 parts; |
| Greenish lily bulb juice | 0.5 to 5 parts; |
| Fig juice | 0.5 to 5 parts; |
| Water chestnut juice | 0.5 to 5 parts; |
| Grosvenor momordica fruit extract | 0.05 to 0.1 parts; |
| Grosvenor momordica fruit | 0.5 to 5 parts; |
| Southern almond | 0.5 to 5 parts; |
| Northern almond | 0.5 to 5 parts; |
| Crystal sugar | 5 to 10 parts; and |
| Honey | 5 to 10 parts. |

6. A composition for reducing phlem and relieving cough in a human in need thereof consisting essentially of the following components by weight,

| | |
|---|---|
| Pear juice | 5 to 15 parts; |
| Apple juice | 25 to 35 parts; |
| Greenish lily bulb juice | 0.5 to 5 parts; |
| Fig juice | 0.5 to 5 parts; |
| Water chestnut juice | 0.5 to 5 parts; |
| Grosvenor momordica fruit extract | 0.05 to 0.1 parts; |
| Grosvenor momordica fruit | 0.5 to 5 parts; |
| Southern almond | 0.5 to 5 parts; |
| Northern almond | 0.5 to 5 parts; and |
| Honey | 5 to 10 parts. |

7. A composition for reducing phlem and relieving cough in a human in need thereof consisting essentially of the following components by weight,

| | |
|---|---|
| Pear juice | 5 to 15 parts; |
| Apple juice | 25 to 35 parts; |
| Greenish lily bulb juice | 0.5 to 5 parts; |
| Fig juice | 0.5 to 5 parts; |
| Water chestnut juice | 0.5 to 5 parts; |
| Grosvenor momordica fruit extract | 0.05 to 0.1 parts; |
| Grosvenor momordica fruit | 0.5 to 5 parts; |
| Southern almond | 0.5 to 5 parts; |
| Northern almond | 0.5 to 5 parts; |
| Crystal sugar | 5 to 10 parts; and |
| Honey | 5 to 10 parts. |

8. A method for reducing phlem and relieving cough in a human in need thereof consisting essentially of administering to the human a therapeutically effective amount of the composition of claim 1.

* * * * *